(12) United States Patent
Betancourt et al.

(10) Patent No.: US 7,158,887 B2
(45) Date of Patent: Jan. 2, 2007

(54) FLUIDS CHAIN-OF-CUSTODY

(75) Inventors: Soraya Sofia Betancourt, Cambridge, MA (US); Oliver C. Mullins, Ridgefield, CT (US); Ahmed Hammami, Edmonton (CA); John Allan Nighswander, Katy, TX (US); Peter S. Hegeman, Stafford, TX (US); John Ratulowski, Missouri City, TX (US); Moin Muhammad, Edmonton (CA); Raymond G. Kennedy, Sherwood Park (CA); Chengli Dong, Sugar Land, TX (US); Erwan Olliero, Macae (BR)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/904,862

(22) Filed: Dec. 1, 2004

(65) Prior Publication Data
US 2005/0165554 A1    Jul. 28, 2005

Related U.S. Application Data

(60) Provisional application No. 60/526,817, filed on Dec. 4, 2003.

(51) Int. Cl.
*G01V 1/40*      (2006.01)
*E21B 47/10*   (2006.01)

(52) U.S. Cl. ............................ 702/11; 73/152.18

(58) Field of Classification Search .............. 702/11, 702/12, 22, 23, 27, 30; 73/152.18, 152.23, 73/152.27, 152.28; 166/250.17, 264; 175/58
See application file for complete search history.

(56) References Cited

U.S. PATENT DOCUMENTS

| 5,303,775 | A | * | 4/1994 | Michaels et al. | ........... 166/264 |
| 5,377,755 | A |   | 1/1995 | Michaels et al. |  |
| 5,394,339 | A | * | 2/1995 | Jones | ........................ 702/12 |
| 5,517,427 | A | * | 5/1996 | Joyce | ........................ 702/50 |
| 6,343,507 | B1 | * | 2/2002 | Felling et al. | ........... 73/152.19 |

(Continued)

FOREIGN PATENT DOCUMENTS

WO        2003064046 A1     8/2003

(Continued)

OTHER PUBLICATIONS

Williams, J.M., Fluid Sampling Under Adverse Conditions, May-Jun. 1998, Revue De L'Iinstitut Francais Du Petrole, vol. 53, No. 3, pp. 355-365.*

(Continued)

*Primary Examiner*—John Barlow
*Assistant Examiner*—Toan M. Le
(74) *Attorney, Agent, or Firm*—Winstead, Sechrest & Minick P.C.; Bryan P. Galloway; Jaime A. Castano

(57) ABSTRACT

A method of assuring the collection of reliable and quality fluid sample includes the steps of acquiring a fluid sample at a point of acquisition, analyzing physical and chemical properties of the fluid sample at the point of acquisition; recording the point of acquisition sample properties in an electronic database archive, analyzing physical and chemical properties of the fluid sample at a location remote from the point of acquisition, recording the remote location sample properties in the archive, validating the fluid sample through comparison of the point of acquisition sample properties and the remote location sample properties and recording the validated sample properties in the archive.

35 Claims, 4 Drawing Sheets

U.S. PATENT DOCUMENTS

| | | |
|---|---|---|
| 6,352,110 B1 | 3/2002 | Langseth et al. |
| 6,543,535 B1 | 4/2003 | Converse et al. |
| 6,549,854 B1 | 4/2003 | Malinverno et al. |
| 6,609,067 B1 * | 8/2003 | Tare et al. .................... 702/9 |
| 6,655,457 B1 | 12/2003 | Dybdahl |
| 6,672,386 B1 * | 1/2004 | Krueger et al. .......... 166/252.5 |
| 6,714,872 B1 * | 3/2004 | DiFoggio et al. ............. 702/12 |
| 6,799,117 B1 * | 9/2004 | Proett et al. .................. 702/12 |
| 6,925,392 B1 * | 8/2005 | McNeil et al. ................ 702/22 |
| 6,964,301 B1 * | 11/2005 | Hill et al. .................... 166/264 |
| 6,965,816 B1 * | 11/2005 | Walker ........................ 701/16 |
| 2002/0020215 A1 | 2/2002 | Nelson et al. |
| 2002/0129936 A1 | 9/2002 | Cernosek |
| 2003/0182061 A1 | 9/2003 | Ferworn et al. |
| 2004/0098202 A1 | 5/2004 | McNeil, III et al. |

FOREIGN PATENT DOCUMENTS

| | | |
|---|---|---|
| WO | 2004106942 A2 | 12/2004 |

OTHER PUBLICATIONS

"The World Anti-Doping Code, International Standard for Testing", Version 3.0, Jun. 2003, World Anti-Doping Agency.

* cited by examiner

FLUIDS CHAIN-OF-CUSTODY

RELATED APPLICATIONS

This application claims the benefit of priority under 35 U.S.C. §119 of U.S. Provisional Application Ser. No. 60/526,817, filed 4 Dec. 2003, entitled FLUIDS CHAIN OF CUSTODY, which is incorporated by reference herein.

FIELD OF THE INVENTION

The present invention relates to fluid characterization and more particularly to a fluids chain-of-custody to facilitate data quality, management and consistency.

BACKGROUND

The term flow assurance is used to describe a broad array of issues related to the reliability and operability of oil and gas production systems. The flow assurance workflow consists of two streams, a design stream and a surveillance stream. The design stream starts in the exploration and appraisal phase and ends with the commissioning of the system. The surveillance stream starts with first production and continues through the producing life of the field. The surveillance stream is a feedback loop used to monitor and optimize the production system performance.

Fluid samples from hydrocarbon reservoirs are essential to understand the fluids to be produced. Many decisions for field development, such as production strategies and design of fluid handling facilities are based on the fluid properties of samples from exploratory wells. It is important to have information of the original fluids in the reservoir. Fluid samples are also acquired at later stages in the life of the reservoir to evaluate the conditions of the fluids at a certain point of time or after some production activities, however, the point of comparison is always the original fluid properties. Thus, it is important to acquire quality, representative fluid samples and to manage this data.

SUMMARY OF THE INVENTION

In view of the foregoing and other considerations, the present invention relates to fluid characterization and more particularly a method of assuring acquisition of a reliable and representative fluid sample. The invention is described herein with reference to reservoir fluids and reservoir characterization, however, it should be recognized that the invention is applicable to any fluid sample such as for use in medical characterizations.

Accordingly, a method of assuring the acquisition of a representative fluid sample is provided. The method includes the steps of acquiring a fluid sample at a point of acquisition that could be downhole (at reservoir depth), at the wellhead or at the surface or subsurface production facility, analyzing physical and chemical properties of the fluid sample at the point of acquisition; recording the point of acquisition sample properties in an electronic database archive, analyzing physical and chemical properties of the fluid sample at a location remote from the point of acquisition, recording the remote location sample properties in the archive, validating the fluid sample through comparison of the point of acquisition sample properties and the remote location sample properties, including reproducing the downhole measurement techniques at the remote location, and recording the validated sample properties in the archive.

Validation of the fluid sample desirably means that selected physical and chemical properties analyzed at the point of acquisition match, within a pre-selected tolerance range of discrepancy, with the sample properties analyzed at a remote location, preferably using the same physical or chemical techniques. However, in certain cases the point of acquisition sample properties may not match the remote location sample properties within the selected tolerance range, in which case the validated sample properties includes identification of the discrepancy in results in the archive. "Analyzed" includes properties measured or obtained through testing. It should also be noted that the validated sample properties may include analysis results which were obtained at a remote location and not at the point of acquisition.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein.

DETAILED DESCRIPTION

Figure 1:
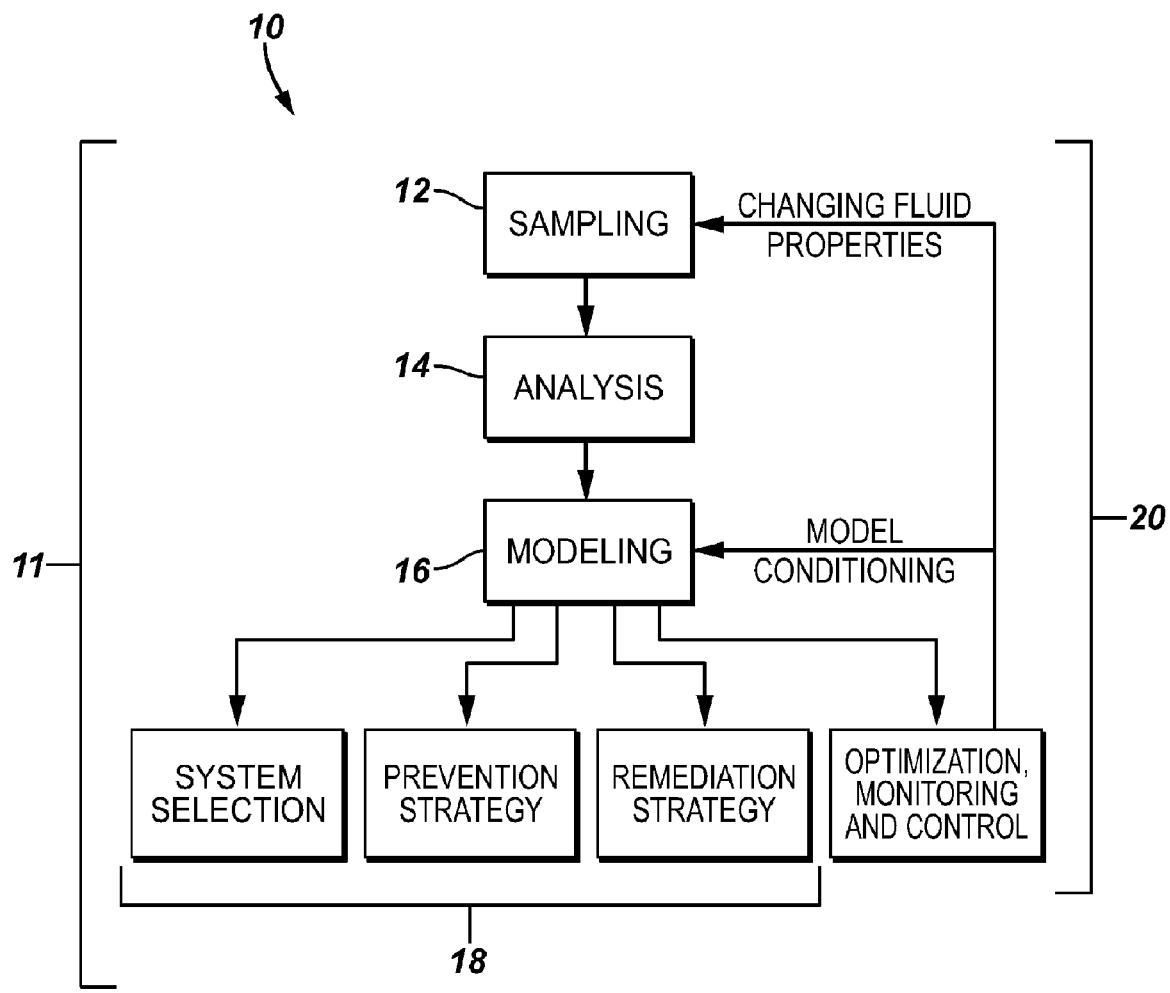
FIG. 1 is a diagram a typical flow assurance process.

Refer now to the drawings wherein depicted elements are not necessarily shown to scale and wherein like or similar elements are designated by the same reference numeral through the several views.

Flow assurance is a critical issue that must be addressed early in the design process for production systems and is vital for offshore production systems. FIG. 1 is a diagram of a typical flow assurance process, generally designated by the numeral 10. Flow assurance process 10, as shown in FIG. 1, broadly illustrates the design process 11 including the steps of sampling 12, analysis 14, modeling 16 and design 18; and the surveillance process 20.

The process starts in the exploration and appraisal phase where in-situ fluid property data are measured and selected fluid samples are retrieved for more detailed analysis. Specific flow assurance related studies may be run on the fluid samples in the laboratory. The scope and type of these analyses will depend on the anticipated problems. The laboratory data is then used in a series of engineering software tools to model various scenarios for the production system. From that process, each system and its appropriate flow assurance management strategy is defined.

Once the selected system is designed and installed, the flow assurance management processes should be monitored and optimized in a surveillance process. Recognizing that the initial design of these strategies was most likely conservative, there are typically good opportunities to optimize the process. However, the large cost of failure requires a careful monitoring of the system to catch potential problems before they result in a catastrophic failure. In the surveillance process, system data like temperatures, pressures and flow rates are collected from sensors at various points. Models that used fluid property data obtained in the design phase are conditioned to the measured system data. These models can now be used to determine the current state of the system and to optimize the system through a series of runs.

The design and surveillance work streams should fit seamlessly together and must be consistent. The same data sets and models used for the system design should be used for monitoring and optimization. In the following, we will describe each element of the workflow process in more detail.

Figure 2:
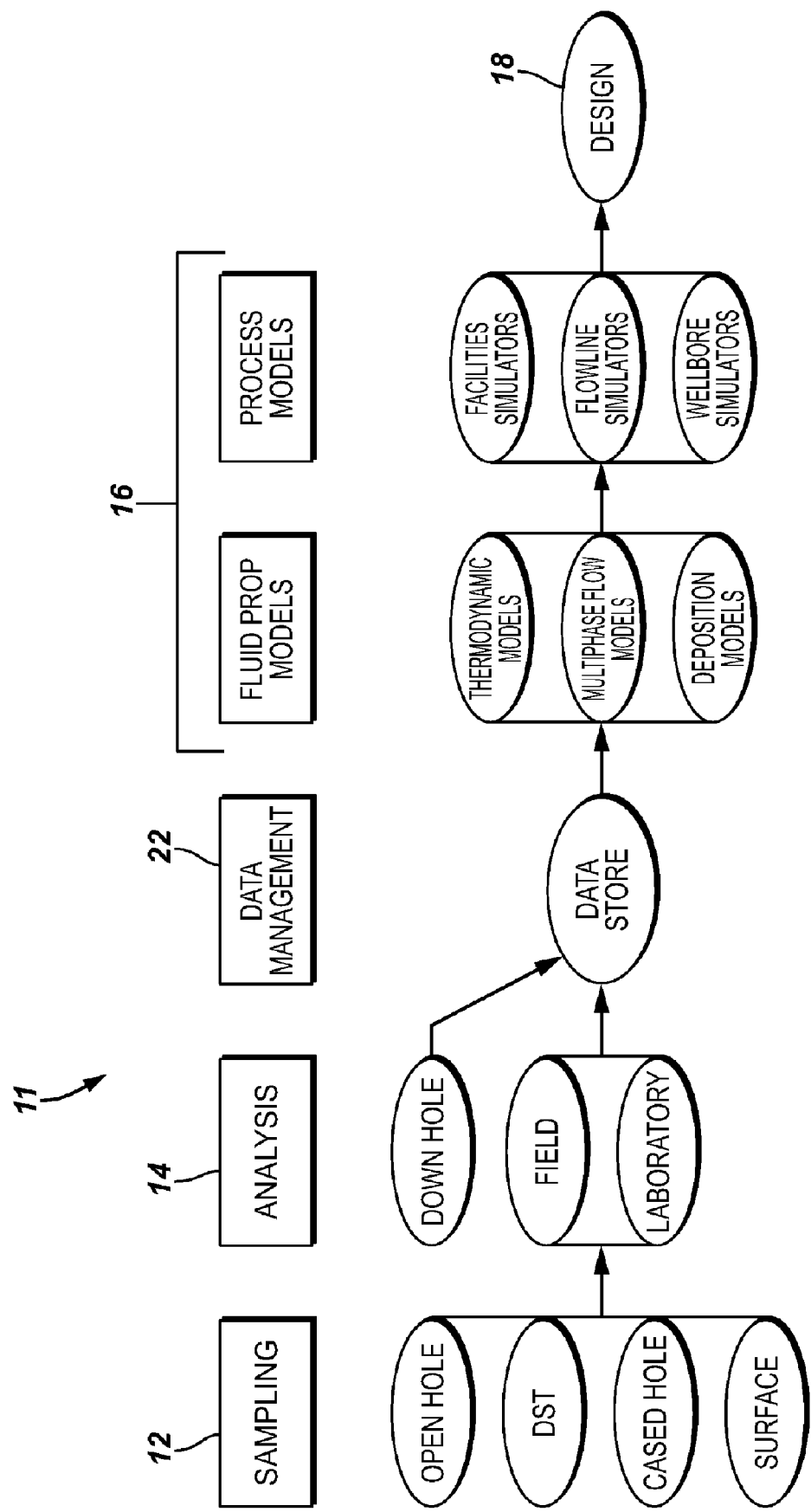
FIG. 2 is a diagram of a design process of a flow assurance process.

FIG. 2 is a diagram of a design process 11 of the present invention. Sampling 12 is the first step in design process 11.

Flow assurance measurements have led to a new awareness of the need to have representative samples. The goal of any sampling procedure is to bring a sample back to the lab that is identical in composition to the fluid in the reservoir. Unfortunately, many of the solids that cause flow assurance problems come out of solution during the sampling process just as they do in production systems. Changes in pressure and temperature can cause phase changes that lead to sample alteration. Introduction of contaminates during the sample acquisition process can also alter the fluid composition. The most common source of contamination is from drilling fluids.

The perfect sample would be collected contamination free from the reservoir at constant temperature and pressure and transported intact to the laboratory maintaining both temperature and pressure. In this way alteration associated with phase changes, transfers or contamination is eliminated. In practice, this is not possible today. A more realistic goal is to reduce the potential for phase changes through pressure and temperature compensation.

The sample data such as, but not limited to, date of sample, serial number, sample number, log file, depth of sample, sampling method and tool configuration, formation pressure, formation temperature, mud type, type of sample bottle, sample temperature and pressure at time of bottling, fluid sample composition, gas-oil ratio (GOR), level of contamination, density, viscosity, $H_2S$ concentration, saturation pressure, water pH, and spectroscopic fingerprinting of the sample (visible-near-infrared (VI-NIR), fluorescence, reflectance) may be recorded. This data may be stored in the data management system 22. Data management system 22 may be a software based, electronic system.

At the analysis stage 14, relevant flow assurance related fluid properties of the samples are measured. The fluid analysis can be done downhole, in the field and/or in the laboratory. The list of relevant fluid properties will vary depending on the type of fluid and the expected system operating conditions. Typically, a phased approach to the design of an analysis program is taken. Sample conditioning and validation is done first. This usually consists of composition and basic fluid properties. Once samples of sufficient quality are identified, flow assurance screening is done.

Examples of wax, asphaltene and hydrate screening are illustrated. For wax, the following are measured on a dead oil: the normal paraffin distribution, using high temperature gas chromatography (HTGC), wax appearance temperature, viscosity and pour point. If these parameters indicate potential wax deposition, elevated viscosity or gelling problems, a more thorough analysis program including measurements made under live oil line conditions and chemical evaluation is needed.

For asphaltenes, dead oil characterization data including SARA (Saturate Aromatic Resin Asphaltene) and paraffinic solvent (typically n-pentane or n-heptane) titration endpoint are used as screens for fluid stability. Because asphaltene screening and modeling capability is less well developed than those for wax, it is common to measure at least one live oil asphaltene precipitation pressure as well. If an asphaltene issue is identified, additional studies are defined to map out the Asphaltene phase diagram as a function of temperature and to evaluate the effectiveness of chemicals or coatings as prevention strategies.

For hydrates gas, composition from a standard PVT or validation study and water composition are used in a thermodynamic model to generate the expected hydrate formation boundary. If the compositional data are unusual or the pressure and temperature conditions are outside the range of validity of the model, direct measurement of hydrate formation conditions may be performed. If a potential problem exists a combination of models and experimental data are used to evaluate the performance of thermodynamic inhibitors and/or low dosage inhibitors (LDHI).

The area of flow assurance measurements is still a developing field with new technologies becoming available regularly. This has both positive and negative consequences. On the positive side, the ability to measure and interpret changes in fluid behavior is continually improving. This leads to a better design that both optimizes performance and reduces flow assurance risks. However, the dynamic nature of the measurement technology has led to a lack of standardization and inconsistencies between measurements and modeling.

In data management 22, all sampling and fluid analysis data are stored in a central database, such as a web-based system. The database may contain sampling logs, transfer and shipping information, and all downhole, field and laboratory fluid property measurements. Database management provides several functions: management of data and a data management service to clients; a web based data delivery system for client data and reports; ability to track sample quality by easily comparing multiple measurements made during the sampling, handling and analysis process and by tracking the sample history (this is a chain-of-custody service); and it can transfer data directly to the fluid property models.

The modeling step 16 may include fluid property models and process models. Fluid property models include, but are not limited to, thermodynamic, deposition and multiphase flow models. Fluid property models are the connection between the analytical fluid data and the engineering application. All of these models use measured data available in the fluid property database. For the thermodynamic model experimental data for fluid properties and phase behavior are loaded into the thermodynamic package. Equations of state parameters are tuned to match the measured values. The model parameters may then be stored in the database along with the fluid properties used to generate them. Deposition and multiphase flow models use fluid property data in the database directly. Again it is important to remember that models should have been developed using the same type of experimental data stored in the database. That is, sample type and quality and analytical technique and procedure of the data must be consistent with that used to develop the models. With the data management process and integrated approach of the present invention this is assured.

Fluid property models are embedded in industry standard engineering packages. Packages used to design production systems include, but are not limited to: reservoir simulators; well bore simulators; flow line simulators and process or facilities simulators. Much effort has been directed towards incorporation of the same set of fluid property models across the different types of simulators. In this way, fluid properties will be modeled consistently in the various parts of the production system.

In design step 18, the models are utilized in the pre-feed and feed stages of engineering design to select the type of production system and develop operational procedures. At this stage, prevention and remediation strategies for common flow assurance problems are developed. Part of the study may include procedures for start up and shut down. In the detailed design phase the models may be revisited and adjusted to reflect the final system design.

Figure 3:
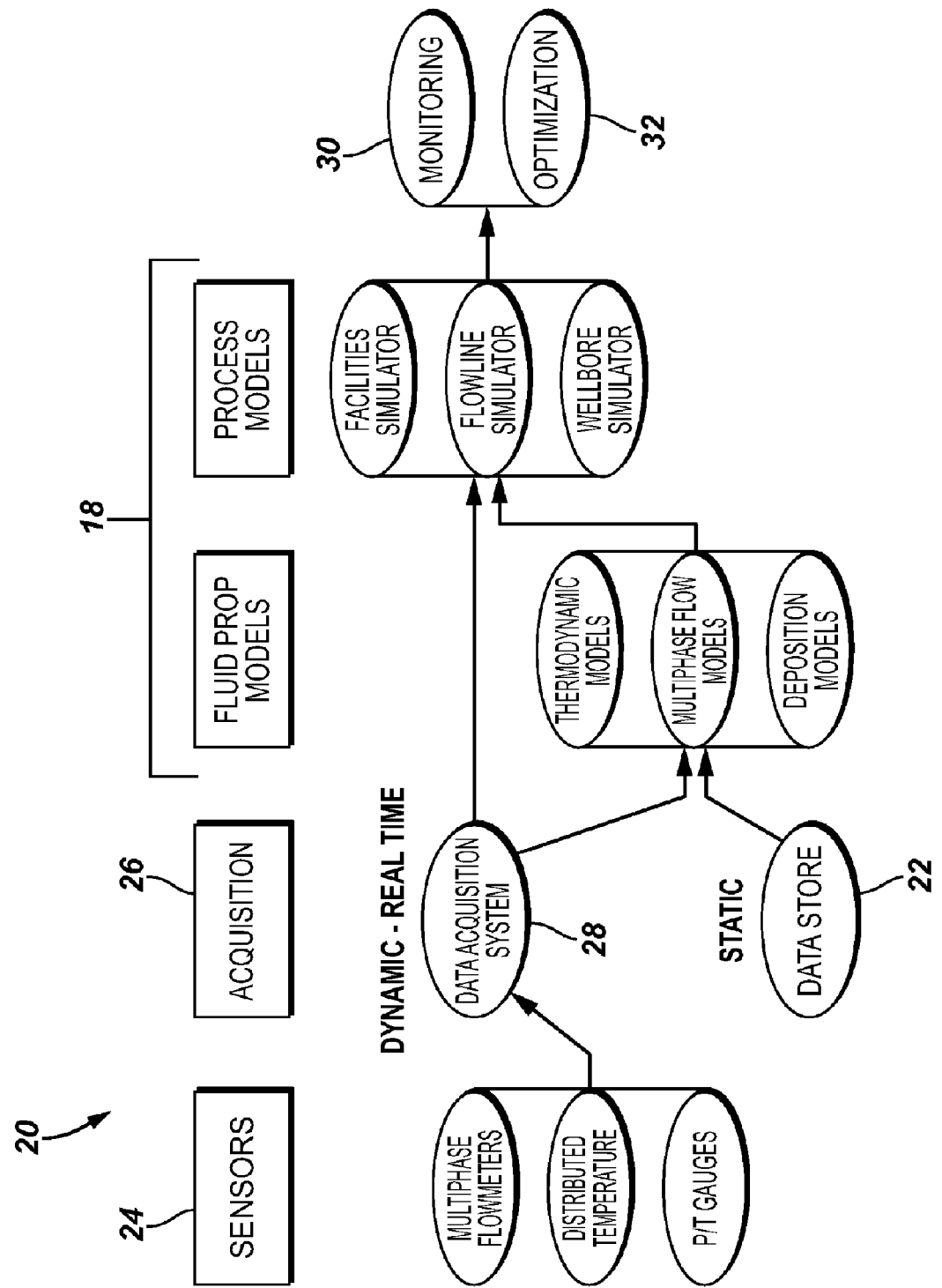
FIG. 3 is a diagram of a surveillance process of a flow assurance process.

FIG. 3 is a diagram of a surveillance process 20 of a flow assurance process of the present invention. Surveillance 20 starts with first production and continues throughout the producing life of the field. It is initially based on the data and models used in design process 11. These models and data may change over time to reflect changes in the system or fluids.

Data is acquired 26 from two sources. Sensors 24 within the system measure data related to system performance (dynamic-real time data). These measurements may be real time or periodic. A variety of sensors 24 are currently available that are important to flow assurance monitoring. They include discrete pressure points, discrete and distributed temperature, phase flow rates and chemical injection rates. These measurements are stored in a database 28.

The second source of data is fluid property and flow assurance data (static data) collected prior to the design stage 11 and maintained in a static data store 22. As in the design stream 11, fluid property data in the static store 22 must be complete and consistent with the models used for surveillance. That implies that well before the system is ever installed one must consider how flow assurance strategies will be monitored 30 and optimized 32. It is essential to take all the required data as wells are drilled and representative samples can be obtained easily. Once the system is on production it is much more difficult and costly to collect high quality flow assurance samples within the subsea domain.

If fluid composition changes over time, the static fluid property data still may be periodically updated. Composition may change during depletion. For example, as a gas condensate falls below the saturation pressure both the condensate yield and the wax appearance temperature may fall. In a compositionally graded accumulation, composition may change as fluids from regions away from the initial sample point are produced. New fields or zones being brought into an existing production system can also change the fluid properties within the system. The fluid property data set must be updated to reflect these changes.

The same engineering models 18 used to design the system are used to interpret the performance of the system. The models must be conditioned to the measured data. The less data available for the system the less constrained the conditioning or tuning will be, thus increasing the uncertainty associated with the non-unique nature of conditioned model.

Consider the following simple example. Inlet and outlet temperature of a section of flowline are different than predicted by the model. Is the overall heat transfer coefficient, U value, along the length of the line uniformly different from the assumed value or is there a smaller section along the flowline where the insulation has failed and elsewhere the assumed U value is appropriate? This may have implications for wax deposition. If the heat transfer coefficient is significantly higher over a short section of flowline there will be a much lower wall temperature in this region, which would lead to an enhanced wax deposition rate. A distributed temperature measurement (temperature every few meters) along the flowline would supply more detail and be able to eliminate or confirm this possibility. Therefore, additional resolution in temperature data results in a conditioned model with less uncertainty.

Figure 4:
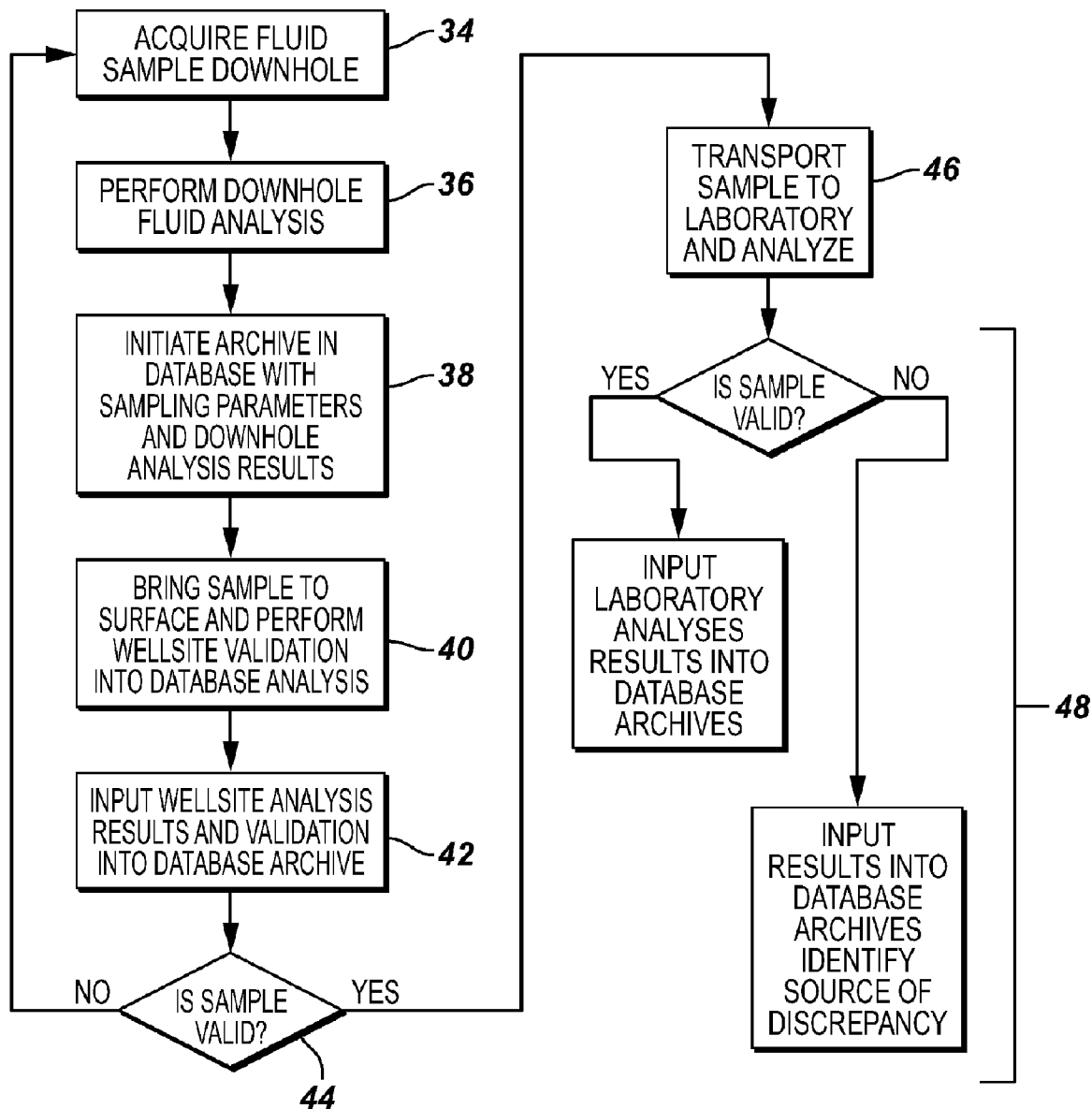
FIG. 4 is a flow chart of a fluids chain-of-custody of the present invention.

FIG. 4 is a flow chart of a fluids chain-of-custody of the present invention. Chain-of-custody refers to the process by which fluid samples are acquired and properties are measured to obtain valuable information for reservoir development. The process includes monitoring fluid property measurements at different stages between and during sample collection and laboratory analysis. More specifically a purpose of the invention is to link downhole, subsea, wellsite, surface facility, and laboratory analyses results into a single data management system, and to facilitate quality control and quality assurance.

A fluids chain-of-custody method begins with acquiring 34 a fluid sample. The fluid sample may be obtained at reservoir depth (downhole), at the wellhead, or at a separator. Measurement 36 in-situ of select physical and chemical properties of the fluid sample are performed. As the sample is collected and analyzed at the point of acquisition an archive 38 is created in an electronically accessible database containing a chain-of-custody page, a display of the downhole measurements (summary and graphical displays) with a link to log files, display of the schematic of the petrophysical logs indicating the location of the sample within the reservoir, and a quality assurance page. Wellsite validation and analysis 40 of the sample is performed at the surface, including the condition of the container and container opening pressure. Measurement techniques used at the point of acquisition are repeated at this stage to detect any anomaly in the measurements with reduced uncertainty. Wellsite measurements and analysis are input and documented in the sample database archive 42. If anomalies are noted between the downhole fluid (in-situ) sample measurements and the wellsite fluid sample measurements, the process may be restarted 44. The validated fluid sample is then transported to a laboratory and analyzed 46. Basic analyses are repeated, and specialized studies may be performed. Although different physical techniques may be used to measure fluid properties at the point of acquisition, for downhole samples the same procedures as used in the downhole environment are repeated at the wellsite and/or the laboratory to evaluate the quality of the sample, the downhole instruments, and the sampling and handling procedures. All the collected data is input in the sample archive in the database for correlation and validation, step 48. Any discrepancies or anomalies can be noted in the archive for utilization in the flow assurance modeling. At each stage of the process the fingerprint of the sample is checked.

The method of the present invention is described in further detail below. The database facilitates the monitoring of the procedures to ensure the quality of the information obtained. Fluid property measurements at different stages are displayed in a web-based system for sample quality tracking and analysis. Procedures are also defined for handling conflicting measurements and investigating the causes of the discrepancy. These guidelines are used as the basis for assessments and audits of chain-of-custody procedures to certify fluid samples and measurements, and select with more confidence the fluid property values to be used for reservoir studies.

Numerous methods may be utilized to obtain the downhole fluid sample(s). The Modular Formation Dynamics Tester (MDT), from Schlumberger, is widely used to acquire downhole fluid samples, and through recent developments performs downhole fluid analysis based on optical spectroscopy methods that enable an early recognition of the fluid characteristics that may affect the acquisition of quality samples. An advantage of downhole fluid analysis is that the fluid is assayed at conditions that are closer to the reservoir conditions, where the fluid has been minimally disturbed from its original conditions. Also, scanning fluid properties at different depths within a geological accumulation prior to the capture of the sample is useful to identify the best sampling depths.

In addition to absorption spectroscopy, other physical techniques may be used to measure fluid properties in the wellbore environment, such as, but not limited to viscosity and density with electro-mechanical systems, dew detection with fluorescence spectroscopy, bubble point pressure with acoustic methods, concentration of hydrogen sulfide with sensors, gas detection with light reflection, pH measurement with chemical reagents and resistivity.

During or immediately after sample acquisition, the wireline sampling tool data channels are processed to extract the recorded and analyzed physical and chemical properties, of the fluid sample at the point of acquisition, such as, but not limited to: "basic information"—date, bottle serial number, sample number, log file name, depth, sampling tool configuration, formation pressure, maximum temperature recorded or formation temperature, mud type, type of sample, type of bottle, bottle opening time, bottle closing time, bottle opening pressure, bottle closing pressure, sample volume, minimum pressure during sample collection, minimum temperature during sample collection; "sample composition"—% by weight of $CO_2$, $C_1$, $C_{2-5}$, $C_{6+}$, $H_2S$, gas-oil ratio (GOR), water fraction in the bottle, and apparent hydrocarbon density; "fluid properties"—viscosity, density, bubble point pressure, asphaltene onset pressure, phase transitions, and resistivity; "contamination"—OBM contamination, $CO_2$ decontaminated, $C_1$ decontaminated, $C_{2-5}$ decontaminated, and $C_{6+}$ decontaminated; "phase transition indicators"—fluorescence plot, gas detector plot, SDS, SAS, and optical downhole camera; and "quality assurance parameters"—optical absorption spectrum, fluorescence spectrum, viscosity, density, bubble point pressure and gas detector.

The output of the data processing algorithm is a "Summary Report" that can easily be uploaded into a fluid database. Since the sample acquisition and downhole analysis information are the first steps in the fluid characterization process, they initialize a new archive in the database for the particular reservoir being sampled. Successive measurements done either at the wellsite, surface facility, or at the laboratory are input in this archive once they become available. A "Chain-of-Custody" page is also initialized in the sample archive displaying the validating parameters at the different stages (downhole, subsea, wellsite, surface, laboratory) to facilitate sample follow-up and process tracing.

Graphical displays of the downhole data are also loaded into the database since they facilitate the analysis and comparison with laboratory measurements. Useful displays include fluid composition, GOR, flowing pressure and temperature versus time, OBM contamination monitoring, fluorescence and gas flag versus time, optical channels, and petrophysical logs identifying the sampling locations.

At a given sampling location one or more bottles may be filled with fluid. It is very important for chain-of-custody to identify correctly the bottles through the serial numbers for traceability at later stages. The database facilitates comparison between samples taken at the same depth, and this may be used as another quality control check.

When the sample reaches the surface, basic Pressure-Volume-Temperature (PVT) laboratory-quality analyses may be performed at the wellsite with PVT Express, from Schlumberger, or other analyses mechanisms, while the downhole fluid analyzer is available to acquire more samples if necessary. The first activity done is the validation of the sample by measuring the sample bottle opening pressure. A value below the indicated sample bottle closing pressure, taking in consideration temperature changes, during the sample acquisition implies that some of the contents of the bottle may have leaked.

If bottle opening pressure validation is satisfactory then wellsite fluid analyses will continue, when planned, otherwise the sample will be transferred to the laboratory. The fluid composition, the GOR and the OBM contamination will be measured and compared with downhole measurements. If fluid properties at downhole and at the wellsite or the laboratory disagree, and if no leakage (difference in bottle opening and closing pressures) has been detected, phase transition may be investigated (i.e., sub-sample used for testing may not have been representative). If no phase transition is detected, repeat the downhole measurements in the laboratory to discard problems with tool calibration. All of these validation processes will be stored and commented in the database.

Basically, there are five situations that may render a sample invalid, namely loss of color (loss of components or phase transitions), loss of gas, loss of components, light scattering and disagreement in a channel-by-channel comparison of the optical spectrum. Comparison of optical spectra obtained at downhole condition and in the laboratory gives all the information, and therefore, it is important for chain-of-custody to repeat the same measurements either at the wellsite or at the laboratory using a properly reconditioned sub-sample.

Downhole techniques are reproduced in the laboratory or the wellsite and displayed in the quality assurance section in the database. The laboratory will measure the composition of the fluid with gas and liquid chromatography, or other composition measurement devices. The comparison of the results of different techniques is very instructive. Also the optical absorption spectrum can be measured in the laboratory or at the wellsite with a replica of the downhole spectrometer, or with a different spectrometer.

Replicating downhole measurements in the laboratory or at the wellsite not only validates the samples and certifies compliance with the chain-of-custody, but also helps in the identification and early correction of other problems such as hardware failures, interpretation problems, and inappropriate sampling, sample reconditioning and/or sample transfer techniques.

From the foregoing detailed description of specific embodiments of the invention, it should be apparent that a chain-of-custody process that is novel has been disclosed. Although specific embodiments of the invention have been disclosed herein in some detail, this has been done solely for the purposes of describing various features and aspects of the invention, and is not intended to be limiting with respect to the scope of the invention. It is contemplated that various substitutions, alterations, and/or modifications, including but not limited to those implementation variations which may have been suggested herein, may be made to the disclosed embodiments without departing from the spirit and scope of the invention as defined by the appended claims which follow.

What is claimed is:

1. A method of assuring acquisition of a representative fluid sample, the method comprising the steps of:
   acquiring a fluid sample at a point of acquisition;
   analyzing physical and chemical properties of the fluid sample at the point of acquisition;
   recording the point of acquisition sample properties in an electronic database archive;
   analyzing physical and chemical properties of the fluid sample at a location remote from the point of acquisition;
   recording the remote location sample properties in the archive;
   validating the fluid sample through comparison of the point of acquisition sample properties and the remote location sample properties;
   recording the validated sample properties in the archive; and
   providing a chain-of-custody page by the archive displaying validating parameters for the fluid sample.

2. The method of claim 1, wherein the point of acquisition is proximate a reservoir formation.

3. The method of claim 1, wherein the remote location is at a wellsite from which the fluid sample was acquired.

4. The method of claim 1, wherein the remote location is at a laboratory.

5. The method of claim 1, wherein the analyses of the fluid sample at the remote location includes replicating the analyzing techniques utilized to obtain the point of acquisition sample properties.

6. The method of claim 1, further including the steps of:
   recording in the archive information regarding the transfer of the sample between physical locations.

7. The method of claim 1, wherein the point of acquisition sample properties includes:
   location of point of acquisition;
   maximum temperature of point of acquisition during sample acquisition;
   closing pressure of sample bottle at point of acquisition; and
   identification of the sample bottle acquired.

8. The method of claim 7, wherein the point of acquisition sample properties further includes:
   sample composition; and
   phase transition indicators.

9. The method of claim 1, wherein the validation step includes comparing a closing pressure of a sample bottle at the point of acquisition with an opening pressure of the sample bottle at the remote location, compensated for temperature variation, for determination of a pressure difference within a pre-selected discrepancy tolerance range.

10. The method of claim 1, wherein the validating step includes recording information regarding discrepancies between the point of acquisition sample properties and the remote location sample properties.

11. The method of claim 1, wherein the archive is web-based.

12. The method of claim 2, wherein the analyses of the fluid sample at the remote location includes replicating the analyzing techniques utilized to obtain the point of acquisition sample properties.

13. The method of claim 2, wherein the point of acquisition sample properties includes:
   location of point of acquisition;
   maximum temperature of point of acquisition during sample acquisition;
   closing pressure of sample bottle at point of acquisition; and
   identification of the sample bottle acquired.

14. The method of claim 2, wherein the point of acquisition sample properties includes:
   location of point of acquisition;
   maximum temperature of point of acquisition during sample acquisition;
   closing pressure of sample bottle at point of acquisition;
   identification of the sample bottle acquired;
   sample composition, and
   phase transition indicators.

15. The method of claim 2, wherein the validation stop includes comparing a closing pressure of a sample bottle at the point of acquisition with an opening pressure of the sample bottle at the remote location, compensated for temperature variation, for determination of a pressure difference within a pre-selected discrepancy tolerance range.

16. The method of claim 13, wherein the validation step includes comparing a closing pressure of a sample bottle at the point of acquisition with an opening pressure of the sample bottle at the remote location, compensated for temperature variation, for determination of a pressure difference within a pre-selected discrepancy tolerance range.

17. The method of claim 1, further including the step of designing a hydrocarbon production system utilizing the validated sample properties.

18. The method of clam 17, further including the steps of monitoring the hydrocarbon production system utilizing the validated sample properties.

19. A method of assuring acquisition of a representative fluid sample, the method comprising the steps of:
   acquiring a fluid sample at a point of acquisition;
   analyzing physical and chemical properties of the fluid sample at the point of acquisition;
   recording the point of acquisition sample properties in an electronic database archive;
   analyzing physical and chemical properties of the fluid sample at a first location remote from the point of acquisition;
   recording the first remote location sample properties in the archive;
   validating the fluid sample through comparison of the point of acquisition sample properties and the first remote location sample properties;
   recording the first remote location sample properties;
   analyzing physical and chemical properties of the fluid sample at a second location remote from the point of acquisition;
   recording the second remote location sample properties in the archive;
   validating the fluid sample through comparison of the point of acquisition sample properties and the second remote location sample properties;
   recording the validated sample properties in die archive; and
   providing a chain-of-custody page by the archive displaying validating parameters for the fluid sample.

20. The method of clam 19, wherein the remote location is at a wellsite from which the fluid sample was acquired.

21. The method of claim 19, wherein the remote location is at a laboratory.

22. The method of claim 19, wherein the analyses of the fluid sample at the first and second remote location includes replicating the analyzing techniques utilized to obtain the point of acquisition sample properties.

23. The method of claim 22, further including the steps of:
  performing specialized tests on the fluid sample at at least one of the remote locations; and
  recording the results of the specialized tests in the archive.

24. The method of claim 22, wherein the validation step includes comparing a closing pressure of a sample bottle at the point of acquisition with an opening pressure of the sample bottle at the remote location, compensated for temperature variation, for determination of a pressure difference within a pre-selected discrepancy tolerance range.

25. The method of claim 22, wherein the point of acquisition sample properties includes:
  location of point of acquisition;
  maximum temperature of point of acquisition during sample acquisition;
  closing pressure of sample bottle at point of acquisition; and
  identification of the sample bottle acquired.

26. The method of claim 23; wherein the point of acquisition sample properties includes:
  location of point of acquisition;
  maximum temperature of point of acquisition during sample acquisition;
  closing pressure of sample bottle at point of acquisition; and
  identification of the sample bottle acquired.

27. The method of claim 19, wherein the validation step includes comparing a closing pressure of a sample bottle at the point of acquisition with an opening pressure of the sample bottle at the remote location, compensated for temperature variation, for determination of a pressure difference within a pre-selected discrepancy tolerance range.

28. The method of claim 19, wherein the point of acquisition sample properties includes:
  location of point of acquisition;
  maximum temperature of point of acquisition during sample acquisition;
  closing pressure of sample bottle at point of acquisition; and
  identification of the sample bottle acquired.

29. The method of claim 19, further including the step of designing a hydrocarbon production system utilizing the validated sample properties.

30. The method of claim 29, further including the steps of monitoring the hydrocarbon production system utilizing the validated sample properties.

31. A method of assuring acquisition of quality fluid samples for flow assurance of a hydrocarbon production system, the method comprising the steps of:
  acquiring a fluid sample at a point of acquisition;
  analyzing physical and chemical properties of the fluid sample at the point of acquisition;
  recording the point of acquisition sample properties in a web-based electronic database archive;
  analyzing physical and chemical properties of the fluid sample at a location remote from the point of acquisition;
  recording the remote location sample properties in the archive;
  validating the fluid sample through comparison of the point of acquisition sample properties and the remote location sample properties;
  recording the validated sample properties in the archive.

32. The method of claim 31, further including the step of providing a chain-of-custody page by the archive displaying validating parameters for the fluid sample.

33. The method of claim 31, further including the step of designing a hydrocarbon production system utilizing the validated sample properties.

34. The method of claim 33, further including the steps of monitoring the hydrocarbon production system utilizing the validated sample properties.

35. The method of claim 31, further including the step of providing a chain-of-custody page by the archive displaying validating parameters for the fluid sample.

* * * * *